United States Patent [19]

Pieper

[11] Patent Number: 4,721,628

[45] Date of Patent: Jan. 26, 1988

[54] METHOD OF CORRECTING UNCLEAR FINGERPRINTS

[76] Inventor: Oscar R. Pieper, 135 Meadowood Dr., Portola Valley, Calif. 94025

[21] Appl. No.: 832,976

[22] Filed: Feb. 25, 1986

[51] Int. Cl.⁴ .............................................. A61B 5/10
[52] U.S. Cl. ...................................... 427/1; 156/230; 156/237; 156/277; 156/278; 427/401
[58] Field of Search .................................. 427/1, 401; 156/DIG. 20, 277, 230, 237, 278; 428/343; 283/81

[56] References Cited

U.S. PATENT DOCUMENTS

| | | | |
|---|---|---|---|
| 2,736,114 | 2/1956 | Krueger | 283/81 |
| 3,290,059 | 12/1966 | Newman | 283/81 |
| 3,661,625 | 5/1972 | Lamers | 283/81 |

OTHER PUBLICATIONS

Klafter, "Pressure Sensitive Labels–Some New Types and New Uses" in Business Forms Reporter, 1966.

Primary Examiner—Janyce A. Bell
Attorney, Agent, or Firm—Jackson & Jones

[57] ABSTRACT

The fingerprints on a fingerprint card having separate uniform areas for receiving the prints of the separate fingers is examined for unclear prints. A nontransparent sheet of paper having an adhesive on one side and an area substantially matching the uniform area is placed over any area containing on unclear print and the finger represented by the unclear print is then reprinted onto the sheet.

2 Claims, 3 Drawing Figures

METHOD OF CORRECTING UNCLEAR FINGERPRINTS

BACKGROUND OF THE INVENTION

1. Field of the Invention

The present invention is directed to an improved method of correcting unclear fingerprints and, more particularly, to a method of enabling a fingerprint operator to replace one or more defective prints on a fingerprint identification card while saving the clear prints.

2. Description of the Prior Art

The art of fingrprinting and identifying persons by their fingerprints is well known. Both ink and inkless method of taking a person's fingerprints are in widespread use. Either a colored ink or a colorless reagent is applied to the persons fingertips and subsequently the fingers are rolled (or pressed) onto a clean recording surface, such as paper, to deposit the ink or reagent on the surface in a pattern corresponding to the fingerprints of the persons. In the inkless method, an additional chemical or reagent is applied to the surface to develop the print so that it is visible. See, for example, U.S. Pat. No. 4,262,623 assigned to the assignee of the present application.

Fingerprint identification is an exacting science which requires the comparison of the pattern of ridge endings and ridge bifurcations (minutiae) of each person's fingerprint. Such comparison may be accomplished manually or by an Automatic Fingerprint Reader System ("AFRS"). Whether the prints are read by machine or by a trained expert, the clarity of the print is obviously of paramount importance. Unclear prints may be caused by (1) an uneven distribution or coating of the ink or other chemical, (2) excessive or insufficient coating of the chemical, (3) improper movement of the finger on the card or (4) improper lifting of the finger from the card after it is rolled. Whatever the cause, an unclear print cannot be accurately read manually or automatically.

Fingerprint cards have been standardized by many governmental agencies such as the U.S. Federal Bureau of Investigation. Such standardized cards are arranged with areas of uniform size (i.e. 1.6"×1.5") for the prints of the individual fingers of each hand. While the goal in taking a person's fingerprints is to provide a clear and legible print of each fingertip, such goal is frequently not realized in the first attempt. An illegible print results in a rejected card. It has been reported that the U.S. Federal Bureau of Investigation processed about seven million prints during 1985 with a rejection rate of approximately 17%. Rejected cards pose an unnecessary burden on the originating and receiving agencies.

In the past, an unclear print of one finger has necessitated starting over with a new card and retaking the prints of all of the person's finger. This operation is time consuming, both for the operator and the person whose fingerprints are being taken. The disadvantages of the prior art methods have been overcome by the present invention.

SUMMARY OF THE INVENTION

In accordance with the present invention, the prints on a fingerprint card having separate uniform areas for the separate fingers, are examined to determine which, if any, print is unclear. A substantially nontransparent sheet (e.g. of paper) having an adhesive material on one side thereof and having an area substantially equal to said uniform area is selected for each unclear print. The sheet with the adhesive side down is then placed over the area containing the defective finger print and the corresponding finger with a fingerprinting chemical thereon is then rerolled over the sheet to provide a new fingerprint. Alternatively, the operator may reprint the finger on the sheet and then place the sheet over the area containing the defective print.

The features of the present invention, which are believed to be novel, are set forth with particularly in the appended claims. The present invention, both as to its organization and operation, thereof, may be best understood by reference to the following description, taken in connection with the accompanying drawings.

BRIEF DESCRIPTION OF THE PREFERRED EMBODIMENT

Figure 1:
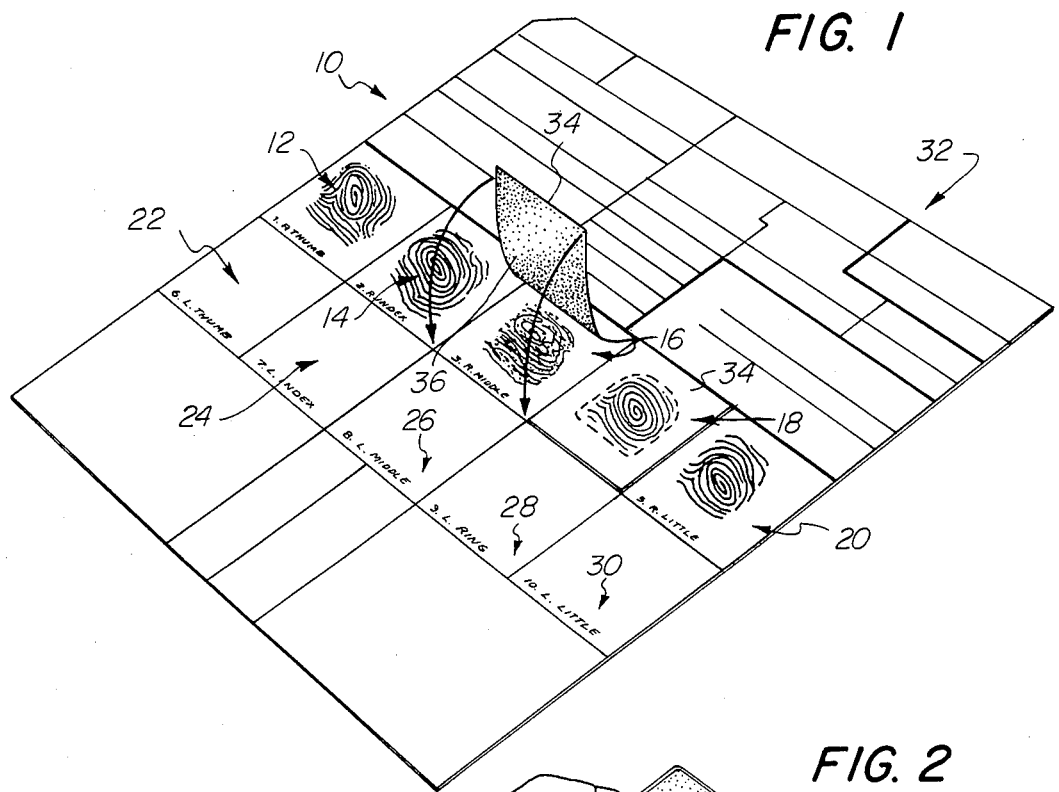
FIG. 1 is a perspective view of a standard fingerprinting card having separate uniform areas thereon for receiving the individual prints of a person's finger.

Referring now to FIG. 1, there is illustrated a standard fingerprint card 10 of the type used by many governmental agencies. The card contains ten separate prearranged areas 12-30 of uniform size (e.g. 1.6" wide by 1.5" high) for receiving the prints of the individual fingers of each hand of the person being fingerprinted. The card also contains a group of separate spaces generally indicated at 32 above the areas 12-30 on which the identification of the person being fingerprinted is to be typed or written. The spaces below the areas 12-30 may be used for receiving additional prints such as the prints of all four fingers of one hand simultaneously. As is illustrated, prints of the fingers of a person's right hand have been placed on the areas 12-22.

Figure 2:
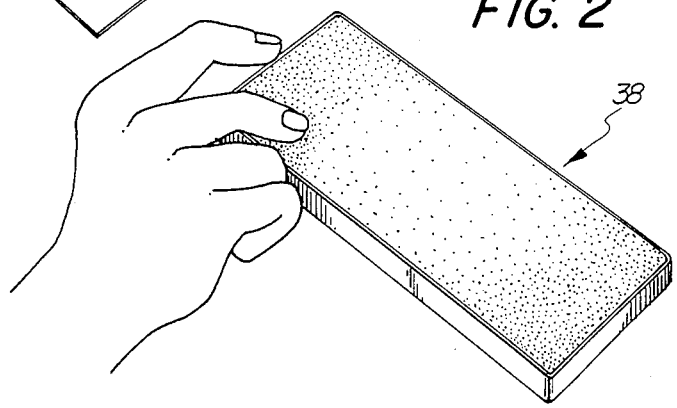
FIG. 2 is a perspective view of an ink (or reagent) pad for providing the chemical to form a fingerprint on the card of FIG. 2.

The print in the area 16 is illustrated as smuged or unclear. In accordance with the present invention, a nontransparent sheet 34, with adhesive 36 affixed to the back thereof, is placed over the smudged print as is illustrated in FIG. 1. Fingerprint chemical, such as ink, from a pad 38 of FIG. 2 particular is then placed on the finger represented by the smudged or otherwise unclear print and the finger is then rerolled on the front side of the sheet 34. A sheet 34 with a new print thereon is illustrated as covering the area 18. Alternatively, the operator may reroll the finger on the sheet 34 and then secure the sheet over the smudged print.

The sheet 34 must have an opacity sufficient to mask out the bad fingerprint impression. Fingerprint cards designed to be read by an AFRS have an acceptable range of thicknesses. As a result, the nontransparent sheets 34 must have a thickness of about 0.002 inches to enable an AFTR to handle th cards with one or more sheets 34 affixed thereto. Only one sheet 34 may be overlayed over a fingerprint space.

Figure 3:
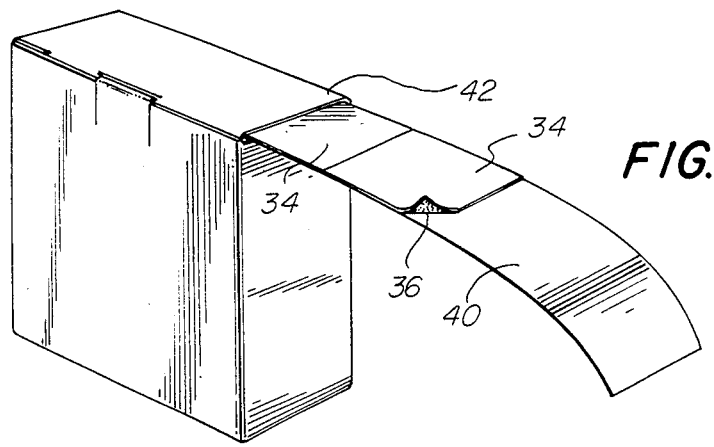
FIG. 3 is a perspective view of a box containing a roll of separate nontransparent sheets affixed to strip of release paper.

Referring now to FIG. 3, the nontransparent sheets may be affixed to a release paper 40 and placed in a roll which is contained a suitable box 42. The box 42 is provided with an opening 44 at the top portion thereof so that the release paper and sheets may be removed from the box as needed.

A novel method of correcting unclear fingerprints has been described. The method enables an operator to save the ledgible prints as well as the fingerprint card by enabling the operator to retake only the unclear print, or prints, on the same card. The nontransparent sheets 34 are permenantly affixed to the fingerprint card 10 so that the card may be stored and read as needed by machines or a fingerprint expert. The scope of the present invention should be measured from the following claims.

What is claimed is:

1. A method of correcting smudged or unclear fingerprints on a fingerprint card having separate uniform areas for the prints of each of the fingers comprising:
    (a) examining the prints placed on the card to determine which prints are defective;
    (b) selecting one of a plurality of uniform substantially nontransparent sheets having an adhesive material on one side thereof and configured to match one of said areas, said sheets having a thickness of about 0.002 inch;
    (c) placing the sheet with the adhesive side down over the area containing the defective print; and
    (d) placing a fingerprinting chemical on the finger for which the defective print was made and rolling the finger over the sheet to provide a new fingerprint.

2. A method of correcting smudged or unclear fingerprints on a fingerprint card having separate uniform areas for the prints of each of the fingers comprising:
    (a) examining the prints placed on the card to determine which print is defective;
    (b) selecting one of a plurality of substantially nontransparent sheets configured to overlay one of said areas and having an adhesive material on one side thereof with a release paper secured to the adhesive, said sheets having a uniform thickness of about 0.002 inch;
    (c) placing a fingerprinting chemical on the finger for which the defective print was made;
    (d) rerolling the finger over the side of the sheet opposite the adhesive to provide a new print on the sheet; and
    (e) placing the sheet with the adhesive side down over the area containing the defective print.

* * * * *